United States Patent [19]

Levine et al.

[11] 4,290,902

[45] Sep. 22, 1981

[54] OXYMOLYBDENUM DIALKYLDITHIOPHOSPHATES AND LUBRICANTS CONTAINING SAME

[75] Inventors: Stephen A. Levine, Fishkill; William R. White, Wappingers Falls, both of N.Y.

[73] Assignee: Texaco Inc., White Plains, N.Y.

[21] Appl. No.: 99,680

[22] Filed: Dec. 3, 1979

[51] Int. Cl.$^3$ ............................................. C10M 1/48
[52] U.S. Cl. ............................ 252/32.7 E; 252/46.7; 260/429 R
[58] Field of Search ............. 252/32.7 E, 46.7; 260/429 R

[56] References Cited

U.S. PATENT DOCUMENTS

| | | | |
|---|---|---|---|
| 3,219,676 | 11/1965 | Wilkinson | 252/32.7 E X |
| 3,400,140 | 9/1968 | Rowan et al. | 252/32.7 E X |
| 3,402,188 | 9/1968 | Wiese | 252/32.7 E X |
| 3,423,316 | 1/1969 | Dickert, Jr. et al. | 252/32.7 E |
| 3,446,735 | 5/1969 | Wiese | 252/32.7 E |
| 3,562,159 | 2/1971 | Mastin | 252/32.7 E |
| 3,840,463 | 10/1974 | Froeschmann et al. | 252/32.7 E X |
| 3,888,776 | 6/1975 | Silverstein | 252/32.7 E X |
| 3,925,213 | 12/1975 | Froeschmann et al. | 252/32.7 E X |
| 4,208,292 | 7/1980 | Bridger | 252/32.7 E |

*Primary Examiner*—Andrew Metz
*Attorney, Agent, or Firm*—Carl G. Ries; Robert A. Kulason; Henry W. Archer

[57] ABSTRACT

This specification relates to novel oxymolybdenum dialkyldithiophosphates having the generic formula $[(RO)_2PS_2]_2Mo_2O_4$, wherein R is a hydrocarbyl group having 1 to 30 carbon atoms. It also relates to the use of these compounds in lubricants as extreme pressure, antiwear, and oxidation-inhibiting additives.

23 Claims, No Drawings

OXYMOLYBDENUM DIALKYLDITHIOPHOSPHATES AND LUBRICANTS CONTAINING SAME

BACKGROUND OF THE INVENTION

The instant invention relates to novel molybdenum dialkyldithiophosphates having utility as extreme pressure and antiwear agents, to a novel process for making the subject compounds and lubricants containing same.

PRIOR ART DISCLOSURES

The prior art is already aware of the use of certain molybdenum-containing compounds in lubricants. Already known are the sulfurized oxymolybdenum organophosphoro-dithioates of U.S. Pat. Nos. 3,400,140 and 3,494,866. These compounds are characterized by the generic structure:

$$[(RO)_2PS_2]_2Mo_2S_2O_2$$

wherein R is an alkyl, cycloalkyl, aryl or alkaryl radical. As is apparent from the above formula, the prior art compound have only one molybdenum atom per phosphorodithioate radical. It is believed that much of the antiwear properties of molybdenum compounds is due to reactions involving the molybdenum atoms and sulfur atoms in situ. It would not, therefore, be advantageous to have compounds containing an increases amount of molybdenum incorporated therein, if it meant excluding the sulfur. On the basis of the above theory, it is surprising to find molybdenum compounds which contain less sulfur and perform better.

SUMMARY OF THE INVENTION

The invention provides molybdenum-containing compounds of the formula:

$$[(RO)_2PS_2]_2Mo_2O_4$$

wherein R is a hydrocarbyl radical having from 1 to 30 carbon atoms, preferably an olefinic or branched chain alkyl radical containing above about 7 carbon atoms, such as 8 to 20. These compounds have a molybdenum content preferably ranging from about 11.7 to 20.0 percent.

The invention provides a process for forming a molybdenum containing compound comprising treating an ammonium or alkali metal molybdate with more than the stoichiometric amount of a concentrated hydrohalic acid required to acidify the molybdate salt, at a temperature ranging from ambient to 80° C.; then, adding not more than two moles of phosphorodithioic acid each mole of molybdenum in the molybdate reactant; refluxing the reaction mixture and removing the water of reaction azeotropically.

The invention also provides a composition comprising a lubricating oil or grease containing as an additive with antiwear, extreme pressure and oxidation-inhibiting properties a compound of the formula:

$$[(RO)_2PS_2]_2Mo_2O_4$$

where R is as above.

DISCLOSURE OF BEST MODE OF THE INVENTION

In the process of this invention, an aqueous solution of sodium molybdate in an inert solvent is treated with more than the stoichiometric amount of a concentrated hydrohalic acid than would be required to simply acidify the molybdate salt, perferably hydrochloric acid, at low temperature. The acidified solution is reacted with a dialkylphosphorodithioic acid, and the reaction product is a molybdenum dialkylphosphorodithioate. It is important to use more than one equivalent of hydrohalic acid per equivalent of molybdenum in the molybdate reactant to obtain the maximum molybdenum content.

The reactions believed to occur in the subject process are as follows:

$$Na_2MoO_4 + 3HCl \rightarrow 2NaCl + \tfrac{1}{2}Cl_2 + H_2O + \tfrac{1}{2}H_2Mo_2O_6 \quad (1)$$

$$\tfrac{1}{2}H_2Mo_2O_6 + (RO)_2PS_2H \rightarrow \tfrac{1}{2}[(RO)_2PS_2]_2Mo_2O_4 + H_2O \quad (2)$$

The result is a product which is not a sulfurized molybdenum salt, such as those described in the cited art, but which would and does exhibit the same infrared spectrum between 600 and 4000 cm$^{-1}$. The analytical results for the crude product of equation 2, when the R group is 2 ethylhexyl, are given below:

|  | % Mo | % P | % S |
|---|---|---|---|
| Calculated | 19.9 | 6.43 | 13.3 |
| Found | 18.5 | 6.10 | 11.3 |

The invention is illustrated in non-limiting fashion by the following examples.

EXAMPLE I

Sodium molybdate (121 g. 0.5 moles) is slurried in 200 ml. of toluene at ambient temperatures. To the slurry, 124 ml. (1.5 moles) of concentrated hydrochloric acid is slowly added. The reaction mixture is then warmed to 80° C., at which 177 g. (0.5 moles) of di-(2-ethylhexyl) phosphorodithioic acid is added. The reaction mixture is refluxed for 8 hours and then the water is azeotroped off. The product is filtered and then the filtrate is stripped of the remaining toluene at reduced pressure.

EXAMPLE II

By following the procedure of Example I, oxymolybdenum diisopropylphosphorodithioate is prepared from 1 mole of potassium molybdate diisopropylphosphorodithioic acid.

EXAMPLE III

By following the procedure of Example I, oxymolybdenum di-(n-butyl) phosphorodithioate is prepared from sodium molybdate and di-(n-butyl) phosphorodithioic acid.

EXAMPLE IV

By following the procedure of Example I, oxymolybdenum dinonylphosphorodithioate is prepared from sodium molybdate and dinonylphosphorodithioic acid.

EXAMPLE V

By following the procedure of Example 1, oxymolybdenum di-(n-amyl)phosphorodithioate is prepared from ammonium molybdate amd di-(n-amyl)phosphorodithioic acid.

EXAMPLE VI

By following the procedure of Example 1, oxymolybdenum didecylphosphorodithioate is prepared from sodium molybdate and didecylphosphorodithioic acid.

The reactions of Examples III of U.S. Pat. No. 3,400,140 and U.S. Pat. No. 3,494,866 were carried out to provide a comparison product having the infrared spectrum as described in the above patents and containing 7.5% (w/w) of molybdenum. The reactions of this invention resulted in a product having an identical infrared spectrum and containing 18.5% (w/w) of molybdenum.

The performance of oxymolybdenum phosphorodithioate of Example I (A) and those of the compounds of Example III of U.S. Pat. No. 3,400,140 and of U.S. Pat. No. 3,494,866 (B) were evaluated relative to a commercial zinc phosphorodithioate (C) in a fully formulated gasoline engine motor oil.

| TEST/Oil Cont'g Additive | A | B | C |
|---|---|---|---|
| Zinc, % | — | — | 0.08 |
| Molybdenum, % | 0.03 | 0.05 | — |
| Bench Oxidn. Test, % Vis Incr. | 227 | 243 | TVTM |
| Anti Wear Data | | | |
| 4-Ball Wear (1 hr-1800 rpm-200° F.-40kg) | 0.36 | 0.36 | 0.38 |

1. TVTM — Too viscous to measure.

The evaluations were effected by means of the 4-Ball Wear Test and by the Bench Oxidation Test. In the first test, steel balls of 0.5" diameter are cleaned, dried and locked in position in the test cup. A charge of 10 to 15 cc. of the test lubricant is then put in the test cup. Separate runs of 60 minutes duration are then conducted at a speed of 1800 rpm on the four-ball wear tester. The test load is 40 kilograms and test temperature is 200° F. The wear in terms of microns pei minute is calculated from the average scar diameter (mm.) from a known formula. The values obtained for test lubricant are compared to results from lubricants having known antiwear properties in service. The lower the figure obtained the better the antiwear properties.

The Bench Oxidation Test simulates the oxidative degradation of the Sequence IIIC Test and correlates with it.

For the Sequence IIIC Test, a 1961 Oldsmobile V8 engine is operated continuously for 64 hours under conditions of moderately high speed and load, very high jacket coolant temperature, and lean air-fuel ratio. Every eight hours an oil sample is taken and checked for viscosity at 100° F. The 8 hour used oil samples are checked for 100° F. viscosity to determine the percent vis. increase versus time pattern for the oil. In addition the engine is disassembled and rated for sludge, piston varnish and valve train wear. The lower the value, the better.

In another evalution a sufficient amount of oxymolybdenum di-(2-ethylhexyl)dithiophosphate was added to a fully formulated motor oil containing a commercial friction modifier to result in an oil containing 0.03% by weight of molybdenum. The respective frictional properties were measured in the 4-Ball Friction and Wear Test under the above given conditions with the following results:

| | Final Coefficient of Friction |
|---|---|
| Oil | 0.097 |
| Oil + 0.03% Mo | 0.070 |
| % Difference | 39% greater friction in oil without Mo |

The materials blended into the SE motor oils were evaluated in terms of their ability to decrease friction in the MEFT (Motored Engine Friction Test). This test utilizes a 1974 Ford 351 CID V8 engine mounted on a test stand. The engine oil is maintained at representative operating temperatures for this test, namely at 190° F. and 210° F. The engine is driven by an electric motor drive until a steady speed of 2000 (rpm) revolutions per minute is reached. The amount of torque (or motoring horsepower) required to drive the engine at this speed is determined, the value obtained being measured in inches of oil. The lower the torque value required to drive the engine at 2000 rpm, the more efficient is the crankcase oil composition since it has reduced the internal friction losses in the engine. In this test the compounds of the invention were found to reduce the motoring horsepower by about 10% relative to the fuel oil blend.

A compound of the invention may be employed as a lubricant, per se. This includes using it as an antiwear agent or as an extreme pressure agent. A compound of the invention also may be employed as an additive in any lubricating oil or grease. As an additive, the compound is generally used in a minor amount, e.g., 0.01 to 20%, preferably 0.03 to 10% by weight of additive, or more preferably from 0.03 to 0.18% by weight of molybdenum in the formulation. Therefore, a known petroleum-based lubricant, such as turbine oil, other light oils, SAE 90 gear oil and other heavy oils, or a known synthetic lubricant, such as esters, polyethers and silicones, may have therein a molybdenum-containing compound within the scope of the present invention. Besides the aforementioned molybdenum compound, the lubricating oil or grease may contain conventional additives, such as thickening agents for the production of lubricating greases (e.g., clay, other pigments, alkali metal soaps, alkaline earth, metal soaps or other soaps), corrosion inhibitors, antioxidants, antirust agents, viscosity improvers, pour point depressants, detergents, other extreme pressure agents, other antiwear agents and the like.

Other modes of applying the principle of the invention may be employed, change being made as regards the details described, provided the features stated in any of the following claims or the equivalent of such be employed.

What is claimed is:

1. A compound of the formula:

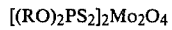

$[(RO)_2PS_2]_2Mo_2O_4$ wherein R is a hydrocarbyl radical having from 1 to 30 carbon atoms, and containing from about 11.7% to about 20.0% of molybdenum.

2. The compound of claim 1, being oxymolybdenum di-(n-butyl)phosphorodithioate.

3. The compound of claim 1, being oxymolybdenum di-(2-ethylhexyl)phosphorodithioate.

4. The compound of claim 1, wherein R ranges from 8 to 20.

5. The compound of claim 1, being oxymolybdenum diisopropylphosphorodithioate.

6. The compound of claim 1, being oxymolybdenum dinonylphosphorodithioate.

7. The compound of claim 1, being oxymolybdenum di-(n-amyl)phosphorodithioate.

8. The compound of claim 1, being oxymolybdenum didecylphosphorodithioate.

9. A process of forming a molybdenum-containing compound comprising treating an ammonium or alkali metal molybdate with more than the stoichiometric amount of a concentrated hydrohalic acid required to simply acidify the molybdate salts, at a temperature ranging from ambient to 80° C.; then, adding not more than two moles of dialkyl phosphorodithioic acid for each mole of molybdenum in the molybdate reactant; refluxing the reaction mixture and removing the water of reaction azeotropically.

10. The process of claim 9, wherein said hydraholic acid is hydrochloric acid and one mole of dialkyl phosphorodithioic acid is added for each mole of molybdenum in said reactant.

11. A composition comprising a lubricating oil or grease containing as an additive with antiwear and extreme pressure properties a compound of the formula:

$$[(RO)_2PS_2]_2Mo_2O_4$$

where R is a hydrocarbyl radical having from 1 to 30 carbon atoms.

12. The composition of claim 11 wherein R ranges from 8 to 20.

13. The composition of claim 11 containing from 0.01 to 20.0 percent by weight of said additive.

14. The composition of claim 11, containing from 0.03 to 10 percent by weight of said additive.

15. The composition of claim 11, containing from 0.03 to 0.18 percent by weight of molybdenum.

16. The composition of claim 11, containing oxymolybdenum di-(n-butyl)phosphorodithioate.

17. The composition of claim 11, containing oxymolybdenum di(2-ethylhexyl)phosphorodithioate.

18. The composition of claim 11, containing oxymolybdenum diisopropylphosphorodithioate.

19. The composition of claim 11, containing oxymolybdenum dinonylphosphorodithioate.

20. The composition of claim 11, containing oxymolybdenum di(n-amyl)phosphorodithioate.

21. The composition of claim 11, containing oxymolybdenum didecylphosphorodithioate.

22. A molybdenum-containing compound prepared by the process comprising treating an ammonium or alkali metal molybdate with more than the stoichiometric amount of a concentrated hydrohalic acid required to simply acidity said molybdate at a temperature ranging from ambient to 80° C.; then adding not more than two moles of dialkyl phosphorodithioic acid for each mole of molybdenum in said molybdate reactant; refluxing the reaction mixture and removing the water of reaction.

23. The compound of claim 22 prepared by adding one mole of dialkyl phosphorodithioic acid for each mole of molybdenum in said reactant.

* * * * *